(12) United States Patent
Okada et al.

(10) Patent No.: US 10,695,274 B2
(45) Date of Patent: Jun. 30, 2020

(54) METHOD FOR PREPARING PERSONAL CARE COMPOSITION COMPRISING SURFACTANT SYSTEM AND HIGH MELTING POINT FATTY COMPOUND

(75) Inventors: Toshiyuki Okada, Singapore (SG); Shoko Maeda, Takatsuki (JP)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 13/617,240

(22) Filed: Sep. 14, 2012

(65) Prior Publication Data

US 2013/0071346 A1   Mar. 21, 2013

Related U.S. Application Data

(60) Provisional application No. 61/534,924, filed on Sep. 15, 2011.

(51) Int. Cl.
| | | |
|---|---|---|
| *A61Q 5/12* | (2006.01) | |
| *A61Q 5/02* | (2006.01) | |
| *A61Q 5/00* | (2006.01) | |
| *A61Q 5/06* | (2006.01) | |
| *A61K 8/34* | (2006.01) | |
| *A61K 8/06* | (2006.01) | |
| *A61K 8/41* | (2006.01) | |

(52) U.S. Cl.
CPC ............ *A61K 8/342* (2013.01); *A61K 8/06* (2013.01); *A61K 8/416* (2013.01); *A61Q 5/12* (2013.01)

(58) Field of Classification Search
CPC .... A61K 8/416; A61K 8/06; A61K 2800/596; A61K 2800/10; A61Q 5/12; A61Q 5/02; A61Q 5/006; A61Q 5/06; A61Q 5/002; A61Q 5/00
See application file for complete search history.

(56) References Cited

U.S. PATENT DOCUMENTS

| | | | |
|---|---|---|---|
| 4,370,272 A | 1/1983 | Wechsler et al. | |
| 4,895,722 A | 1/1990 | Abe et al. | |
| 4,976,956 A | 12/1990 | Noe | |
| 5,932,202 A | 8/1999 | Guskey et al. | |
| 6,399,799 B1 | 6/2002 | Pereira et al. | |
| 8,273,336 B2 | 9/2012 | Yamaki | |
| 8,349,301 B2 | 1/2013 | Wells et al. | |
| 8,367,048 B2 | 2/2013 | Wells et al. | |
| 8,470,305 B2 | 6/2013 | Johnson et al. | |
| 8,828,370 B2 | 9/2014 | Yang et al. | |
| 9,126,057 B2 | 9/2015 | Runglertkriangkrai | |
| 9,308,398 B2 | 4/2016 | Hutton et al. | |
| 2002/0012646 A1 | 1/2002 | Royce et al. | |
| 2002/0015685 A1 | 2/2002 | Pascual et al. | |
| 2002/0110533 A1 | 8/2002 | Huff et al. | |
| 2003/0084519 A1 | 5/2003 | Yang | |
| 2004/0116539 A1 | 6/2004 | Biercevicz et al. | |
| 2004/0157754 A1 | 8/2004 | Geary et al. | |
| 2006/0057096 A1 | 3/2006 | Lazzeri et al. | |
| 2006/0264352 A1 | 11/2006 | Sajic et al. | |
| 2007/0190015 A1 | 8/2007 | Bebot | |
| 2007/0298004 A1 | 12/2007 | Li | |
| 2009/0047231 A1 | 2/2009 | Sazanami et al. | |
| 2009/0324527 A1* | 12/2009 | Okada et al. | 424/70.27 |
| 2009/0324528 A1 | 12/2009 | Okada et al. | |
| 2009/0324529 A1 | 12/2009 | Okada et al. | |
| 2009/0324530 A1 | 12/2009 | Yang et al. | |
| 2009/0324531 A1 | 12/2009 | Okada et al. | |
| 2009/0324532 A1 | 12/2009 | Okada et al. | |
| 2010/0015078 A1 | 1/2010 | Li | |
| 2010/0143280 A1* | 6/2010 | Yokogi et al. | 424/70.27 |
| 2010/0143281 A1 | 6/2010 | Okada et al. | |
| 2010/0143282 A1 | 6/2010 | Yokogi et al. | |
| 2010/0143425 A1 | 6/2010 | Okada et al. | |
| 2010/0150858 A1 | 6/2010 | Runglertkriangkrai | |
| 2011/0045039 A1 | 2/2011 | Sunkel et al. | |
| 2011/0048449 A1 | 3/2011 | Hutton, III et al. | |
| 2011/0104094 A1 | 5/2011 | Lee et al. | |
| 2012/0316239 A1 | 12/2012 | Okada et al. | |
| 2013/0259817 A1 | 10/2013 | Uehara et al. | |
| 2014/0348884 A1 | 11/2014 | Hilvert et al. | |
| 2014/0356307 A1 | 12/2014 | Yang et al. | |
| 2014/0377205 A1 | 12/2014 | Uehara et al. | |
| 2014/0377206 A1 | 12/2014 | Uehara et al. | |

FOREIGN PATENT DOCUMENTS

| | | |
|---|---|---|
| EP | 0472184 B1 | 10/1994 |
| FR | 2943540 B1 | 6/2011 |
| GB | 2220216 A | 1/1990 |
| JP | S63-143935 | 6/1988 |
| JP | H107532 | 1/1998 |
| JP | 2005255627 | 3/2004 |
| JP | 2008231019 A | 10/2008 |
| JP | 4559392 B2 | 10/2010 |
| JP | 5656276 B2 | 1/2015 |
| KR | 20050094289 A | 9/2005 |
| KR | 20050094290 A | 9/2005 |
| WO | WO2009016555 A1 | 2/2009 |
| WO | 2009158440 A2 | 12/2009 |
| WO | WO2010/068400 | 6/2010 |
| WO | 2010077707 A2 | 7/2010 |

OTHER PUBLICATIONS

International Search Report PCT/US2012/055375; dated Feb. 13, 2014; 14 pages.
All final and non-final office actions for U.S. Appl. No. 13/492,173.
All final and non-final office actions for U.S. Appl. No. 14/308,841.
All final and non-final office actions for U.S. Appl. No. 14/308,856.
Benoit, H. https://www.highbeam.com/doc/1G1-76812410.html. Jun. 1, 2001.
Cosmetic Formulation Basics—Hair Conditioner, 2011, http://chemistscorner.com/cosmetic-formulation-basics-hair-conditioners/).

(Continued)

*Primary Examiner* — Tracy Liu
(74) *Attorney, Agent, or Firm* — Linda M. Sivik

(57) ABSTRACT

Disclosed is a method of preparing a personal care composition, comprising a step of mixing a hot oil phase and a cold aqueous phase in a high shear field to form an emulsion, wherein the mixing step is conducted by using a homogenizer having a rotating member, wherein the oil phase contains from 0 to about 50% of the aqueous carrier by weight of the oil phase, and wherein the temperature of the emulsion when formed is from about 10° C. to about 40° C.

8 Claims, No Drawings

(56) References Cited

OTHER PUBLICATIONS

John P Reganold et al: "Expressing cation exchange capacity in milliequivalents per100 grams and in SI units", Journal of Agronomic Education, Jan. 1, 1985 (Jan. 1, 1985), pp. 84-90.
PCT International Search Report and Written Opinion for PCT/US2014/043172 dated Sep. 26, 2014.
PCT International Search Report and Written Opinion for PCT/US2014/043196 dated Sep. 29, 2014.
Richmond, editor, Cationic Surfactants, 1990.
The Personal Formulator; Cetrimonium chloride; catalogue publication date: Jul. 12, 2004. http://www.personalformulator.com/wvss/product_info.php?products_id=1169.
Varisoft 432 PPG (Evonik).

* cited by examiner

METHOD FOR PREPARING PERSONAL CARE COMPOSITION COMPRISING SURFACTANT SYSTEM AND HIGH MELTING POINT FATTY COMPOUND

CROSS REFERENCE TO RELATED APPLICATIONS

This application claims the benefit of U.S. Provisional Application No. 61/534,924 filed on Sep. 15, 2011.

FIELD OF THE INVENTION

The present invention relates to a method of preparing a personal care composition, comprising a step of mixing a hot oil phase and a cold aqueous phase in a high shear field to form an emulsion, wherein the mixing step is conducted by using a homogenizer having a rotating member, wherein the oil phase contains from 0 to about 50% of the aqueous carrier by weight of the oil phase, and wherein the temperature of the emulsion when formed is from about 10° C. to about 40° C.

BACKGROUND OF THE INVENTION

A variety of methods have been developed to prepare personal care composition comprising surfactants and high melting point fatty compounds and aqueous carriers.

A common preparation method for such composition is emulsification. Such emulsification is conducted by a variety of procedures, by a variety of temperatures, and by a variety of homogenizers.

For example, WO 2004/054693 discloses in Example 13, a hair conditioner prepared by the steps: preparing a water phase comprising 46.785% water, 0.3% potassium chloride and 0.1% disodium EDTA at 24-46° C.; preparing an oil (emulsion) phase containing 41.785% water, 0.15% distearyl dimonium chloride, 0.84% cetrimonium chloride, and 3.0% cetyl alcohol at 65-88° C.; delivering the phases through pipes which join eventually leading into a blending tube which is an antechamber section of a Sonolator®; and homogenizing the blend.

WO 2009/158440 relates to a hair conditioning composition containing behenyl trimethyl ammonium methosulfate and having a higher yield point. This publication discloses, at pages 6 and 7, that the composition is preferably substantially free of di-long alkyl cationic surfactants in view of improved wet conditioning benefits.

WO 2010/077707 relates to a method of preparing a personal care composition by direct feeding of an oil phase and/or a water phase into a high shear field. This publication also discloses, at page 10, the composition is preferably substantially free of di-long alkyl cationic surfactants in view of improved wet conditioning benefits.

However, there remains a need for a method for preparing hair conditioning compositions and other personal care compositions which comprise di-long alkyl cationic surfactants, to effectively transform surfactants and fatty compounds to emulsions while not deteriorating wet conditioning benefit.

There may remain a need for such a method, by such effective transformation, to provide personal care compositions with, for example: (i) effective delivery of the conditioning benefits to hair and/or skin, for example, delivery of improved conditioning benefits from the same amount of active ingredients such as surfactants and fatty compounds; (ii) an improved product appearance, i.e., richer, thicker, and/or more concentrated product appearance, and which consumer may feel higher conditioning benefits from its appearance; (iii) homogeneous product appearance which is suitable as products on market; and/or (iv) rheology which is suitable as products on market and/or improved stability of such rheology.

Further, in addition to the above needs, there may exist a need for such a method which provides more flexibility of manufacturing operation and/or require less investment for high pressure.

None of the existing art provides all of the advantages and benefits of the present invention.

SUMMARY OF THE INVENTION

The present invention is directed to a method of preparing a personal care composition, wherein the composition comprises: a cationic surfactant system comprising a mono-alkyl quaternized ammonium salt cationic surfactant and di-alkyl cationic surfactant; a high melting point fatty compound; and an aqueous carrier, wherein the method comprises the steps:
(1) preparing an oil phase comprising the surfactant and the high melting point fatty compound, wherein the temperature of the oil phase is higher than a melting point of the high melting point fatty compound; and
(2) preparing an aqueous phase comprising the aqueous carrier, wherein the temperature of the aqueous phase is below the melting point of the high melting point fatty compounds; and
(3) mixing the oil phase and the aqueous phase to form an emulsion;

wherein the mixing step (3) comprises the following detailed steps:
(3-1) feeding either of the oil phase or the aqueous phase into a high shear field having an energy density of about $1.0 \times 10^2$ J/m$^3$ or more;
(3-2) feeding the other phase directly to the field; and
(3-3) forming an emulsion;
the mixing step (3) is conducted by using a homogenizer having a rotating member;
wherein the oil phase contains from 0 to about 50% of the aqueous carrier by weight of the oil phase; and
wherein the temperature of the emulsion when formed is from about 10° C. to about 40° C.

The methods of the present invention effectively transform surfactants and fatty compounds to emulsions.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

Method of Manufacturing

The present invention is directed to a method of preparing a personal care composition, wherein the composition comprises: a cationic surfactant system comprising a mono-alkyl quaternized ammonium salt cationic surfactant and di-alkyl cationic surfactant; a high melting point fatty compound; and an aqueous carrier, wherein the method comprises the steps:
(1) preparing an oil phase comprising the surfactant and the high melting point fatty compound, wherein the temperature of the oil phase is higher than a melting point of the high melting point fatty compound; and
(2) preparing an aqueous phase comprising the aqueous carrier, wherein the temperature of the aqueous phase is below the melting point of the high melting point fatty compounds; and
(3) mixing the oil phase and the aqueous phase to form an emulsion; wherein the mixing step (3) comprises the following detailed steps:
(3-1) feeding either of the oil phase or the aqueous phase into a high shear field having an energy density of about $1.0 \times 10^2$ J/m$^3$ or more;
(3-2) feeding the other phase directly to the field; and
(3-3) forming an emulsion;
the mixing step (3) is conducted by using a homogenizer having a rotating member;
wherein the oil phase contains from 0 to about 50% of the aqueous carrier by weight of the oil phase; and
wherein the temperature of the emulsion when formed is from about 10° C. to about 40° C.

Preferably, the method further comprises the step of adding additional ingredients such as silicone compounds, perfumes, preservatives, polymers, if included, to the emulsion. Preferably, as described below under the title "GEL MATRIX", the emulsion is a gel matrix.

Details of Mixing Step (3)

In the present invention, by directly feeding the phase to the high shear field, the oil phase and the aqueous phase first meet in the high shear field. It is believed that, by meeting first in the high shear field, the method of the present invention provides improved transformation of surfactants and high melting point fatty compounds to emulsions, i.e., the resulted compositions contain reduced amount of non-emulsified surfactants/high melting point fatty compounds, compared to other methods by which such phases first meet in non- or lower shear field. It is also believed that, by such improved transformation to an emulsion, the method of the present invention provides the resulted composition with improved conditioning benefits, and may also provide them with improved product appearance and/or product stability.

In the present invention, "direct feeding" means, feeding the two phases such that the two phases can reach to the high shear field after first meeting, within 0.52 seconds or less, preferably 0.5 seconds or less, more preferably 0.3 seconds or less, still more preferably 0.1 seconds or less, even more preferably 0 second, in view of improved transformation to emulsions. In the present invention, the direct feeding is preferably conducted by a direct injection.

In the present invention, "high shear field" means that the field has an energy density of from about $1.0 \times 10^2$ J/m$^3$, preferably from about $1.0 \times 10^3$ J/m$^3$, more preferably from about $1.0 \times 10^4$ J/m$^3$ in view of improved transformation to emulsions, and to about $5.0 \times 10^8$ J/m$^3$, preferably to about $2.0 \times 10^7$ J/m$^3$, more preferably to about $1.0 \times 10^7$ J/m$^3$.

In the present invention, it is preferred that the mixing step (3) comprises the following detailed steps:
(3-1) feeding the aqueous phase into a high shear field having an energy density of $1.0 \times 10^2$ J/m$^3$ or more;
(3-2) feeding the oil phase directly to the field; and
(3-3) forming an emulsion.

In the present invention, especially when using homogenizers having a rotating member described below in detail, it is preferred to feed the oil phase into the high shear field in which the aqueous phase is already present, in view of stably manufacturing the compositions with improved conditioning benefits.

Preferably, in the present invention, the mixing step (3) including the detailed steps (3-1) and (3-2) is conducted by using a high shear homogenizer.

It is known that high shear homogenizers include, for example: high shear homogenizers having a rotating member; and high pressure homogenizers. In the present invention, high shear homogenizers having a rotating member are used, rather than high pressure homogenizers such as Sonolator® available from Sonic Corporation, Manton Gaulin type homogenizer available from the APV Manton Corporation, and Microfluidizer available from Microfluidics Corporation. Such a high shear homogenizer having a rotating member is believed to: provide more flexibility of manufacturing operation by its two independent operation levers (flow rate and rotating speed) while high pressure homogenizers have only one lever (pressure determined depending on flow rate); and/or require less investment for high pressure.

High shear homogenizers having a rotating member useful herein include, for example, direct injection rotor-stator homogenizers such as: Becomix® available from A. Berents Gmbh&Co. and Lexa-30 available from Indolaval/TetraPac, in view of improved transforming to emulsions. These direct injection rotor-stator homogenizers are preferred since the two phases can quickly reach to the high shear field after first meeting, compared to other homogenizers having a rotating member, when used as-is. Such other homogenizers having a rotating member include, for example: T. K. pipeline homomixer available from Primix Corporation, and DR-3 available from IKA Corporation. Those other homogenizers having a rotating member might be used with modifications such that the two phases can quickly reach to the high shear field after first meeting. Such other homogenizers having a rotating member, when used as-is, may provide an increased amount of high melting point fatty compound crystals which are not transformed into emulsions, in the composition. Other homogenizers, which has a lower energy density, such as that named T. K. pipeline homomixer may also provide such an increased amount of high melting point fatty compound crystals Details of Temperature Conditions In the present invention, the oil phase has a temperature which is higher than a melting point of the high melting point fatty compounds. Preferably, the oil phase has a temperature which is higher than a melting point of the oil phase. Preferably, the oil phase has a temperature of from about 25° C., more preferably from about 40° C., still more preferably from about 50° C., even more preferably from about 55° C., further preferably from about 66° C., and to about 150° C., more preferably to about 95° C., still more preferably to about 90° C., even more preferably to about 85° C., when mixing it with the aqueous phase.

In the present invention, the aqueous phase has a temperature which is below the melting point of the high melting point fatty compounds. Preferably, the aqueous phase has a temperature of from about 10° C., more preferably from about 15° C., still more preferably from about 20° C., and to about 65° C., more preferably to about 55° C., still more preferably to about 52° C., even more preferably to about 48° C., when mixing it with the oil phase. Preferably, the temperature of the aqueous phase, when mixing it with the oil phase, is at least about 5° C. lower than, more preferably at least about 10° C. lower than the temperature of the oil phase. Preferably, the temperature of the aqueous phase, when mixing it with the oil phase, is from about 2° C. to about 60° C. lower than, more preferably from about 2° C. to about 40° C. lower than, still more preferably from about 2° C. to about 30° C. lower than the melting point of the high melting point fatty compounds.

In the present invention, the temperature of the emulsion when formed is from about 10° C. to about 40° C., even more preferably from about 20° C. to about 37° C., in view of improved rheology consistency and/or stability of emulsion structure. Preferably, especially when forming a gel matrix, the temperature of the emulsion when formed is from about 2° C. to about 60° C. lower than, more preferably from about 2° C. to about 40° C. lower than, still more preferably from about 2° C. to about 30° C. lower than the melting point of the high melting point fatty compounds.

Details of Oil Phase Composition

Oil phase comprises the surfactants and the high melting point fatty compounds. The oil phase comprises preferably from about 50% to about 100%, more preferably from about 60% to about 100%, still more preferably from about 70% to about 100% of the surfactants and the high melting point fatty compounds, by weight of the total amount of the surfactants and the high melting point fatty compounds used in the personal care composition, in view of providing the benefits of the present invention.

The surfactants and the high melting point fatty compounds are present in the oil phase, with or without other ingredients, at a level by weight of the oil phase of, preferably from about 35% to about 100%, more preferably from about 50% to about 100%, still more preferably from about 60% to about 100%, in view of providing the benefits of the present invention.

Oil phase may contain an aqueous carrier such as water and lower alkyl alcohols, and polyhydric alcohols. If included, the level of aqueous carrier in the oil phase is up to about 50%, more preferably up to about 40%, still more preferably up to about 25%, even more preferably up to about 15% by weight of the oil phase, in view of providing the benefits of the present invention. Among the aqueous carrier, it is further preferred to control the level of water in oil phase, such that the level of water in oil phase is preferably up to about 40%, more preferably up to about 25%, still more preferably up to about 15%, even more preferably up to about 10% by weight of the oil phase. The oil phase may be substantially free of water. In the present invention, "oil phase being substantially free of water" means that: the oil phase is free of water; the oil phase contains no water other than impurities of the ingredients; or, if the oil phase contains water, the level of such water is very low. In the present invention, a total level of such water in the oil phase, if included, preferably 1% or less, more preferably 0.5% or less, still more preferably 0.1% or less by weight of the oil phase.

Oil phase may contain other ingredients than the surfactants and the high melting point fatty compounds and aqueous carrier. Such other ingredients are, for example, water-insoluble components and/or heat sensitive components, such as water-insoluble silicones, water-insoluble perfumes, water-insoluble preservatives such as parabens and non-heat sensitive preservatives such as benzyl alcohol. In the present invention, "water-insoluble components" means that the components have a solubility in water at 25° C. of below 1 g/100 g water (excluding 1 g/100 water), preferably 0.7 g/100 g water or less, more preferably 0.5 g/100 g water or less, still more preferably 0.3 g/100 g water or less. If included, it is preferred that the level of such other ingredients in the oil phase is up to about 50%, more preferably up to about 40%, by weight of the oil phase, in view of providing the benefits of the present invention.

Details of Aqueous Phase Composition

Aqueous phase comprises aqueous carrier. The aqueous phase comprises preferably from about 50% to about 100%, more preferably from about 70% to about 100%, still more preferably from about 90% to about 100%, even more preferably from about 95% to about 100% of aqueous carrier, by weight of the total amount of the aqueous carrier used in the personal care composition, in view of providing the benefits of the present invention.

Aqueous carrier is present in the aqueous phase, with or without other ingredients, at a level by weight of the aqueous phase of, from about 50% to about 100%, more preferably from about 70% to about 100%, still more preferably from about 90% to about 100%, even more preferably from about 95% to about 100%, in view of providing the benefits of the present invention.

Aqueous phase may contain the surfactants and high melting point fatty compounds. If included, it is preferred that the level of the sum of the surfactants and high melting point fatty compounds in the aqueous phase is up to about 20%, more preferably up to about 10%, still more preferably up to about 7% by weight of the aqueous phase, in view of providing the benefits of the present invention. Even more preferably, the aqueous phase is substantially free of the surfactants and high melting point fatty compounds. In the present invention, "aqueous phase being substantially free of the surfactants and high melting point fatty compounds" means that: the aqueous phase is free of the surfactants and high melting point fatty compounds; or, if the aqueous phase contains the surfactants and high melting point fatty compounds, the level of such surfactants and high melting point fatty compounds is very low. In the present invention, a total level of such surfactants and high melting point fatty compounds in the aqueous phase, if included, preferably 1% or less, more preferably 0.5% or less, still more preferably 0.1% or less by weight of the aqueous phase.

Aqueous phase may contain other ingredients than the surfactants and the high melting point fatty compounds and aqueous carrier. Such other ingredients are, for example, water soluble components and/or heat sensitive components, such as water soluble pH adjusters, water soluble preservatives such as phenoxyethanol and Kathon®, and water soluble polymers. In the present invention, "water soluble components" means that the components have a solubility in water at 25° C. of at least 1 g/100 g water, preferably at least 1.2 g/100 g water, more preferably at least 1.5 g/100 g water, still more preferably at least 2.0 g/100 water. If included, it is preferred that the level of such other ingredients in the aqueous phase is up to about 20%, more preferably up to about 10% by weight of the aqueous phase, in view of providing the benefits of the present invention.

Personal Care Composition

The personal care composition of the present invention comprises a surfactant, high melting point fatty compound, and aqueous carrier. The surfactants, the high melting point fatty compounds, and the aqueous carrier are in the form of emulsion.

Cationic Surfactant System

The compositions of the present invention comprise a cationic surfactant system. The cationic surfactant system can be included in the composition at a level from about 0.5%, preferably from about 1%, more preferably from about 1.5%, still more preferably from about 1.8%, still more preferably from about 2.0%, and to about 8%, preferably to about 5%, more preferably to about 4% by weight of the composition, in view of providing the benefits of the present invention.

Preferably, in the present invention, the surfactant is water-insoluble. In the present invention, "water-insoluble surfactants" means that the surfactants have a solubility in water at 25° C. of below 1 g/100 g water (excluding 1 g/100 g water), preferably 0.7 g/100 g water or less, more preferably 0.5 g/100 g water or less, still more preferably 0.3 g/100 g water or less.

Cationic surfactant system useful herein comprises a mono-alkyl quaternized ammonium salt cationic surfactant and a di-alkyl cationic surfactant. It is believed that such combination of a mono-alkyl quaternized ammonium salt cationic surfactant and a di-alkyl cationic surfactant provides feel of quick rinse and/or feel of easy to spread through hair, compared to single use of mono-alkyl cationic surfactants which have one long alkyl chain which has from 12 to 30 carbon atoms. In the cationic surfactant system it is preferred that the weight ratio of the mono-alkyl quaternized ammonium salt cationic surfactant to the di-alkyl cationic surfactant is from about 1:1 to about 10:1, more preferably from about 1.5:1 to about 7:1, still more preferably from about 2:1 to about 5:1, in view of stability in rheology and conditioning benefits.

Mono-Alkyl Quaternized Ammonium Salt Cationic Surfactant

The mono-alkyl quaternized ammonium salt cationic surfactants useful herein are those having one long alkyl chain of preferably from 12 to 30 carbon atoms, more preferably from 16 to 24 carbon atoms, still more preferably from 18 to 22 carbon atoms, in view of conditioning benefits. Such mono-alkyl quaternized ammonium salt cationic surfactants useful herein are, for example, those having the formula (I):

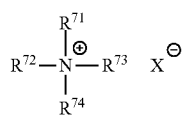

(I)

wherein one of $R^{71}$, $R^{72}$, $R^{73}$ and $R^{74}$ is selected from an aliphatic group of from 12 to 30 carbon atoms, more preferably from 16 to 24 carbon atoms, still more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, one of $R^{71}$, $R^{72}$, $R^{73}$ and $R^{74}$ is selected from an alkyl group of from 12 to 30 carbon atoms, more preferably from 16 to 24 carbon atoms, still more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Among them, more preferred cationic surfactants are those having a longer alkyl group, i.e., C18-22 alkyl group. Such cationic surfactants include, for example, behenyl trimethyl ammonium chloride, methyl sulfate or ethyl sulfate, and stearyl trimethyl ammonium chloride, methyl sulfate or ethyl sulfate.

Di-Alkyl Cationic Surfactant

Di-alkyl cationic surfactants useful herein are those having two long alkyl chains of from 12 to 30 carbon atoms, more preferably from 16 to 24 carbon atoms, still more preferably from 18 to 22 carbon atoms, including, for example, di-long alkyl quaternized ammonium salts. Such di-alkyl quaternized ammonium salts useful herein are those having the formula (I):

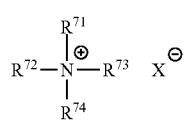

(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The high melting point fatty compound can be included in the composition at a level of from about 0.5%, preferably from about 1.0%, more preferably form about 1.5%, still more preferably from about 2%, even more preferably from about 4%, and to about 15%, preferably to about 10% by weight of the composition, in view of providing the benefits of the present invention.

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present invention, more preferred fatty alcohols are cetyl alcohol, stearyl alcohol and mixtures thereof.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan).

Gel Matrix

Preferably, in the present invention, the emulsion is in the form of a gel matrix. The gel matrix comprises the cationic surfactant system, the high melting point fatty compound, and an aqueous carrier. The gel matrix is suitable for providing various conditioning benefits, such as slippery feel during the application to wet hair and softness and moisturized feel on dry hair.

Preferably, especially when the gel matrix is formed, the total amount of the cationic surfactant and the high melting point fatty compound is from about 1.0%, preferably from about 2.0%, more preferably from about 3.0% by weight of the composition, in view of providing the benefits of the present invention, and to about 15%, preferably to about 14%, more preferably to about 13%, still more preferably to about 10% by weight of the composition, in view of spreadability and product appearance. Furthermore, when the gel matrix is formed, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:4, still more preferably from about 1:2 to about 1:4, in view of providing improved wet conditioning benefits.

Preferably, when the gel matrix is formed, the composition of the present invention is substantially free of anionic surfactants and anionic polymers, in view of stability of the gel matrix. In the present invention, "the composition being substantially free of anionic surfactants and anionic polymers" means that: the composition is free of anionic surfactants and anionic polymers; or, if the composition contains anionic surfactants and anionic polymers, the level of such anionic surfactants and anionic polymers is very low. In the present invention, a total level of such anionic surfactants and anionic polymers, if included, preferably 1% or less, more preferably 0.5% or less, still more preferably 0.1% or less by weight of the composition. Most preferably, the total level of such anionic surfactants and anionic polymers is 0% by weight of the composition.

Aqueous Carrier

The composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 90% water.

Silicone Compound

Preferably, the compositions of the present invention preferably contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

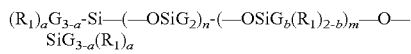

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$$A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —N($CH_3$)$_2$ or —$NH_2$, more preferably —$NH_2$. Another highly preferred amino silicones are those corresponding to formula (I) wherein m=0, a=1, q=3, G=methyl, n is preferably from about 400 to about 600, more preferably about 500; and L is —N($CH_3$)$_2$ or —$NH_2$, more preferably —$NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; and sequestering agents, such as disodium ethylenediamine tetra-acetate; ultraviolet and infrared screening and absorbing agents such as benzophenones; and antidandruff agents such as zinc pyrithione.

Product Forms

The compositions of the present invention can be in the form of rinse-off products or leave-on products, and can be formulated in a wide variety of product forms, including but not limited to creams, gels, emulsions, mousses and sprays. The composition of the present invention is especially suitable for hair conditioners especially rinse-off hair conditioners.

Method of Use

The composition of the present invention is preferably used for a method of conditioning hair, the method comprising following steps:
(i) after shampooing hair, applying to the hair an effective amount of the conditioning composition for conditioning the hair; and
(ii) then rinsing the hair.

Effective amount herein is, for example, from about 0.1 ml to about 2 ml per 10 g of hair, preferably from about 0.2 ml to about 1.5 ml per 10 g of hair.

The composition of the present invention provides improved conditioning benefits, especially improved wet conditioning benefits after rinsing and improved dry conditioning, while maintaining wet conditioning benefit before rinsing. The composition of the present invention may also provide improved product appearance to consumer. Thus, a reduced dosage of the composition of the present invention may provide the same level of conditioning benefits as those of a full dosage of conventional conditioner compositions. Such reduced dosage herein is, for example, from about 0.3 ml to about 0.7 ml per 10 g of hair.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Compositions (wt %)

| | Components | Ex. 1 | Ex. 2 | Ex. 3 | Ex. i | Ex. ii | Ex. iii |
|---|---|---|---|---|---|---|---|
| | Method of preparation | I | I | I | II | I | III |
| 1 | Behenyl trimethyl methosulfate | 1.5 | — | 2.2 | 2.3 | 1.5 | 1.5 |
| 2 | Behenyl trimethyl ammonium chloride | — | 1.3 | — | — | — | — |
| 3 | Varisoft 432 PPG *1 | 0.5 | 0.4 | 0.7 | 0.8 | 0.5 | 0.5 |
| 4 | Cetyl alcohol | 0.9 | 0.8 | 1.2 | 1.2 | 0.9 | 0.9 |
| 5 | Stearyl alcohol | 2.3 | 2.1 | 2.9 | 3.1 | 2.3 | 2.3 |
| 6 | Benzyl alcohol | 0.4 | 0.4 | 0.4 | 0.4 | 0.4 | 0.4 |
| 7 | Deionized Water | — | — | — | — | 7.0 | — |
| 8 | Disodium EDTA | 0.13 | 0.13 | 0.13 | 0.13 | 0.13 | 0.13 |
| 9 | Water-soluble preservatives | 0.03 | 0.03 | 0.03 | 0.03 | 0.03 | 0.03 |
| 10 | Deionized Water | q.s. to 100% of the composition | | | | | |
| 11 | Aminosilicone *2 | 2.0 | 2.0 | 1.5 | 1.5 | 2.0 | 2.5 |
| 12 | Perfume | 1.0 | 0.35 | 0.5 | 0.5 | 0.35 | 1.0 |
| 13 | Panthenol | 0.05 | 0.05 | 0.05 | 0.05 | 0.05 | 0.05 |
| 14 | Panthenyl ethyl ether | 0.03 | 0.03 | 0.03 | 0.03 | 0.03 | 0.03 |
| | Syneresis | O | — | — | — | — | C |
| | Thick feel | O | — | — | — | — | C |
| | Rheology consistency | 1.0-1.2% | — | 0.85% | 9% | — | — |
| | Conditioning | The composition of Ex. 1 shows better wet and/or dry conditioning benefits compared to the composition of Ex. ii. | | | | | |

Definitions of Components
*1 67-69% of Dicetyldimonium Chloride in q.s. to100% Propylene Glycol and 5% water, available from Evonik Goldschmidt Corporation
*2 Aminosilicone: Available from GE having a viscosity 10,000 mPa · s, and having following formula (I): $(R_1)_aG_{3-a}$—Si—$(—OSiG_2)_n$—$(—OSiG_b(R_1)_{2-b})_m$—O—$SiG_{3-a}(R_1)_a$ (I) wherein G is methyl; a is an integer of 1; b is 0, 1 or 2, preferably 1; n is a number from 400 to about 600; m is an integer of 0; $R_1$ is a monovalent radical conforming to the general formula $C_qH_{2q}L$, wherein q is an integer of 3 and L is —$NH_2$ Method of Preparation The above hair conditioning compositions of "Ex. 1" through "Ex. 3" and "Ex. i" through "Ex. iii" were prepared by one of the following Methods I or II as shown above.

Method I

Components 1-7 are mixed and heated to from about 66° C. to about 85° C. to form an oil phase. Separately, Components 8-10 are mixed and heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ J/m³ to $1.0 \times 10^7$ J/m³ where the aqueous phase is already present. The temperature of the gel matrix when formed is from about 20° C. to about 37° C. A gel matrix is formed. If included, Components 11-14 are added to the gel matrix with agitation. Then the composition is cooled down to room temperature.

Method II

Components 1-7 are mixed and heated to from about 66° C. to about 85° C. to form an oil phase. Separately, Components 8-10 are mixed and heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ $J/m^3$ to $1.0 \times 10^7$ $J/m^3$ where the aqueous phase is already present. The temperature of the gel matrix when formed is from about 44° C. A gel matrix is formed. If included, Components 11-14 are added to the gel matrix with agitation. Then the composition is cooled down to room temperature.

Method III

Components 1-10 are mixed with agitation, and heated to about 80° C. The mixture is cooled down to about 55° C. and gel matrix is formed. If included, Components 11-14 are added to the gel matrix with agitation. Then the mixture is cooled down to room temperature.

Properties and Conditioning Benefits

For some of the above compositions, properties and conditioning benefits are evaluated by the following methods. Results of the evaluation are also shown above.

The embodiments disclosed and represented by "Ex. 1" through "Ex. 3" are hair conditioning compositions made by the method of the present invention which are particularly useful for rinse-off use. Such embodiments have many advantages. For example, they effectively transform to emulsions, and provides wet conditioning benefit.

Such advantages can be understood by the comparison between the examples of the present invention and comparative examples "Ex. i" through "Ex. iii". For example, less syneresis was observed in "Ex. 1" of the present invention, compared to a comparative example "Ex. iii" which was prepared by a different method. It is thought that Ex. 1" of the present invention has an improved stability in the emulsion structure, compared to the comparative example "Ex. iii" which was prepared by a different method. Additionally, improved thick feel was observed in "Ex. 1" of the present invention, compared to a comparative example "Ex. iii".

Another example is that the comparison between "Ex. 1" and "Ex. 3" of the present invention and a comparative example "Ex. i" shows that "Ex. 1" and "Ex. 3" made by the method of the present invention have an improved rheology consistency, compared to a comparative example "Ex. i" made by a higher emulsification temperature.

Furthermore, "Ex. 1" of the present invention which contains substantially free of water in the oil phase shows better wet and/or dry conditioning benefits, compared to comparative example "Ex. ii" containing 7% of water in the oil phase.

Syneresis

Syneresis is evaluated by direct visual evaluation of water amount on to the surface of the composition, after the storage at 5° C. for 2 months. Improved stability of the emulsion structure causes less water being squeezed out from the composition.

O: No obvious water observed at the conditioner surface
C: Control (Some water appears on the surface)
C1: Perceived as equal to Control
x: Perceived to provide inferior wet conditioning benefit, compared to Control.

Thick Feel of the Composition

Thick feel is evaluated by panelists, by touching a hair sample after applying 10 ml compositions.

O: Perceived to provide improved thick feel compared to Control.
C: Control
C1: Perceived as equal to Control
x: Perceived to provide inferior thick feel, compared to Control.

Rheology Consistency

Rheology consistency is evaluated by differences in rheology (% difference in rheology between minimum and maximum rheologies) by repeated manufacturing of the same composition. Compositions having a lower % difference is considered to have more consistency compared to those having a higher % difference.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of preparing a personal care composition, wherein the composition comprises: a cationic surfactant system; a high melting point fatty compound having a melting point temperature of a least about 25° C.; and an aqueous carrier, wherein the cationic surfactant is included in the composition at a level from 0.5% to 8% by weight of the composition, wherein the cationic surfactant system comprises a mono-alkyl quaternized ammonium salt cationic surfactant having one long alkyl chain of from about 12 to about 30 carbon atoms and a di-alkyl cationic surfactant having two long alkyl chains of from about 12 to about 30 carbon atoms; and wherein the weight ratio of the mono-alkyl quaternized ammonium salt cationic surfactant to the di-alkyl cationic surfactant is from 2:1 to 5:1; and wherein the method comprises the steps:

(1) preparing an oil phase comprising the surfactant system and the high melting point fatty compound, wherein the temperature of the oil phase is higher than a melting point of the high melting point fatty compound; and (2) preparing an aqueous phase comprising the aqueous carrier, wherein the temperature of the aqueous phase is below the melting point of the high melting point fatty compounds; and
(3) mixing the oil phase and the aqueous phase to form a gel matrix;
wherein the mixing step (3) comprises the following detailed steps:
(3-1) feeding either of the oil phase or the aqueous phase into a high shear field having an energy density of about $1.0 \times 10^2$ J/m$^3$ or more;
(3-2) feeding the other phase directly to the field by direct injection; and
(3-3) forming a gel matrix;
wherein the mixing step (3) is conducted by using a rotor-stator;
wherein the oil phase contains from 0 to about 50% of the aqueous carrier by weight of the oil phase; and
wherein the temperature of the gel matrix when formed is from about 20° C. to about 37° C.

2. The method of claim 1, wherein the mixing step (3) comprises the following detailed steps:
(3-1) feeding the aqueous phase into a high shear field having an energy density of about $1.0 \times 10^2$ J/m$^3$ or more;
(3-2) feeding the oil phase directly to the field by direct injection; and
(3-3) forming a gel matrix.

3. The method of claim 1, wherein the high shear field has an energy density of from about $1.0 \times 10^3$ J/m$^3$.

4. The method of claim 1, wherein the two phases reach to the high shear field within 0.52 seconds or less, after first meeting.

5. The method of claim 1, wherein the level of water in the oil phase is up to about 40% by weight of the oil phase.

6. The method of claim 1, wherein the level of water in the oil phase is up to about 25% by weight of the oil phase.

7. The method of claim 1 wherein the weight ratio of the cationic surfactant system and the high melting point fatty compound is within the range of from about 1:1 to about 1:4.

8. A composition made by the method of claim 1.

* * * * *